United States Patent [19]
Ladjimi

[11] Patent Number: 6,092,908
[45] Date of Patent: Jul. 25, 2000

[54] APPARATUS FOR SELECTIVELY PROVIDING DIFFERENT SHADES OF LIGHT TO ILLUMINATE A GIVEN PATTERN

[75] Inventor: Wannas A. Ladjimi, St Petersburg, Fla.

[73] Assignee: Bigorre Aerospace Corporation, Pinellas Park, Fla.

[21] Appl. No.: 09/159,103

[22] Filed: Sep. 23, 1998

[51] Int. Cl.[7] .................................................. F21V 33/00
[52] U.S. Cl. ........................... 362/133; 362/33; 362/125; 362/231; 362/236; 362/251; 362/362; 362/372; 362/373
[58] Field of Search ................................ 362/11, 29, 125, 362/33, 367, 812, 222–224, 1, 470–472, 133, 231, 236, 251, 362, 372, 373

[56] References Cited

U.S. PATENT DOCUMENTS

| | | | |
|---|---|---|---|
| 1,664,332 | 3/1928 | Slott | 362/1 |
| 3,093,319 | 6/1963 | Gemain | 362/1 |
| 4,236,192 | 11/1980 | Duggan | 362/133 |

*Primary Examiner*—Sandra O'Shea
*Assistant Examiner*—Ismael Negron
*Attorney, Agent, or Firm*—Miles & Stockbridge P.C.; William L. Feeney

[57] ABSTRACT

An apparatus for selectively providing light of different shades as an aid in designing interiors has a housing that is closed except on an operator side. A light subsystem in the interior of the housing has a plurality of light sources. First and second panels within the housing are tack boards allowing fabric to be attached to them. The first panel is downwardly inclined toward the operator side, whereas the second panel is upwardly inclined toward the operator side. The light subsystem includes downwash light sources for illuminating fabric on the first panel so that a human sitting on the operator side can select a shade of white light to be used with a given fabric. The fabric would then be attached to the second panel where an upwash light source illuminates the fabric to confirm the selection of a given shade of white light as best matched to a given fabric.

18 Claims, 3 Drawing Sheets

APPARATUS FOR SELECTIVELY PROVIDING DIFFERENT SHADES OF LIGHT TO ILLUMINATE A GIVEN PATTERN

BACKGROUND OF THE INVENTION

The present invention relates to an apparatus for selectively providing light of different shades as an aid in designing interiors. More specifically, it relates to a system for determining the light that should be used for a given fabric pattern. Even more specifically, the system determines the lighting that should be used in the interior design of an aircraft.

When designing the interior of a room, one often chooses a pattern for the wall. Wall paper may be used on a wall of a room. In similar fashion, fabric patterns can used for the interior of an aircraft cabin.

As customers often realize when they take an item of clothing home from a store, a fabric pattern looks different depending on the light. The pattern may look one way under the lights in the store and may look different under the lights at the customer's home.

Therefore, a pattern and the light for a room should be selected to be compatible.

OBJECTS AND SUMMARY OF THE INVENTION

Accordingly, it is a primary object of the present invention to provide a new and improved apparatus for selectively providing light of different shades as an aid in designing interiors and related method.

A more specific object of the present invention is to provide for selecting lights that best illuminate a given pattern.

A further object of the present invention is to provide for selecting the best light to use with a fabric pattern for an aircraft cabin.

Yet another object of the present invention is to provide for selecting a light that best illuminates a pattern whether the light is below the pattern or above the pattern.

The above and other features of the present invention which will be more readily understood when the following detailed description is considered in conjunction with the accompanying drawings are realized by an apparatus for selectively providing light of different shades as an aid in designing interiors including: a housing having an interior and open at least partly on an operator side; first panel interior to the housing and operable to selectively hold patterned sheet material; a plurality of light sources supported by the housing, each light source operable to output a corresponding shade of light; and a controller operably connected to the housing and operable to selectively turn on the light sources one at a time such that any patterned sheet material on the first panel is illuminated by the shade of light corresponding to the light source turned on at a given moment. The light sources preferably include at least one upwash light source positioned to light patterned sheet material removably secured to the housing, the upwash light source shining light on the patterned sheet material from below the patterned sheet material, and at least one downwash light source positioned to light patterned sheet material removably secured to the housing, the downwash light source shining light on the patterned sheet material from above the patterned sheet material. A second panel is interior to the housing and operable to selectively hold patterned sheet material. The upwash light source is positioned to illuminate any patterned sheet material placed on the second panel and the downwash light source is positioned to illuminate any patterned sheet material placed on the first panel. The downwash light source is one of a plurality of downwash light sources, each of which is positioned to illuminate any patterned sheet material placed on the first panel. The first panel extends downward toward the operator side and the second panel extends upward toward the operator side.

The housing is enclosed on all sides other than the operator side. The first panel is a tack board and the second panel is a tack board. The housing has a height of at least 4 feet. A fan in the housing provides air flow for an operator positioned just outside the housing at the operator side. The controller is operable to dim the light sources. The light sources output different shades of white light.

The invention may alternately be described as an apparatus for selectively providing light of different shades as an aid in designing interiors including: a housing having an interior and open at least partly on an operator side, the housing being enclosed on all sides other than the operator side; first panel interior to the housing and operable to selectively hold patterned sheet material; a light subsystem supported by the housing, the light subsystem operable to selectively output different shades of light; and a controller operably connected to the housing and operably connected to the light subsystem to determine shades of light for illuminating any patterned sheet material on the first panel such that a person on the operator side may view patterned sheet material under different shades of light. The light subsystem includes: at least one upwash light source positioned to light patterned sheet material removably secured to the housing, the upwash light source shining light on the patterned sheet material from below the patterned sheet material; and at least one downwash light source positioned to light patterned sheet material removably secured to the housing, the downwash light source shining light on the patterned sheet material from above the patterned sheet material. A second panel is interior to the housing and operable to selectively hold patterned sheet material. The upwash light source is positioned to illuminate any patterned sheet material placed on the second panel and the downwash light source is positioned to illuminate any patterned sheet material placed on the first panel. The first panel extends downward toward the operator side and the second panel extends upward toward the operator side. The housing is enclosed on all sides other than the operator side.

The invention may alternately be described as a method of selecting lights for use with a patterned sheet material, the steps including: providing an apparatus for selectively providing light of different shades as an aid in designing interiors with: a housing having an interior and open at least partly on an operator side; first panel interior to the housing and operable to selectively hold patterned sheet material; a plurality of light sources supported by the housing, each light source operable to output a corresponding shade of light; and a controller operably connected to the housing and operable to selectively turn on the light sources one at a time such that any patterned sheet material on the first panel is illuminated by the shade of light corresponding to the light source turned on at a given moment; attaching a patterned sheet material on the first panel; and selectively turning the light sources in order for a person on the operator side to view light shining on the patterned sheet material. The patterned sheet material is a fabric. The light source that best illuminates the fabric is selected from the viewing of the fabric under different of the light sources. The light source that best illuminates the fabric is installed in a room having the fabric. The light source that best illuminates the fabric is installed in an aircraft interior having the fabric. The plurality of light sources provide different shades of white light.

BRIEF DESCRIPTION OF THE DRAWINGS

The above and other features of the present invention will be more readily understood when the following detailed description is considered in conjunction with the accompanying drawings wherein like characters represent like parts throughout the several views and in which.

DETAILED DESCRIPTION

Figure 1:
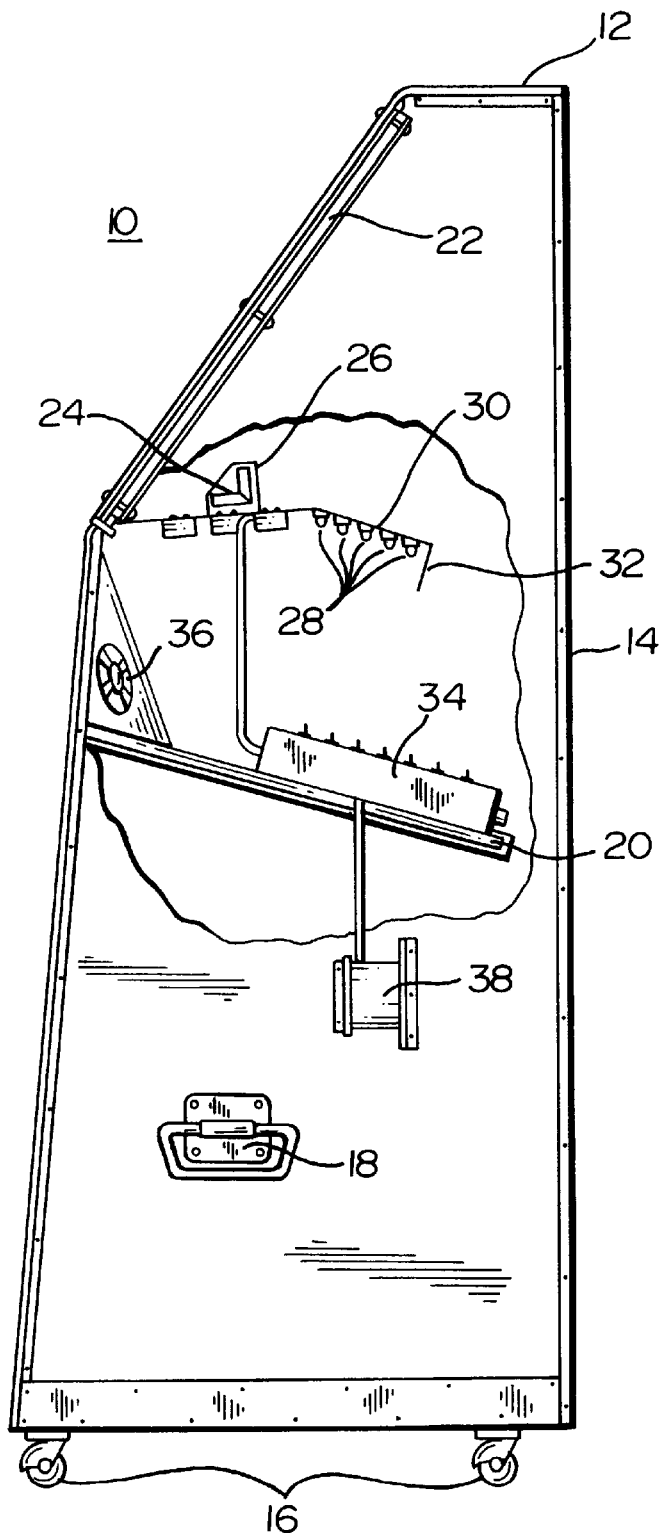
FIG. 1 is a side view of an apparatus for selectively providing light of different shades as an aid in designing interiors according to the present invention and a side section of housing is broken away to illustrate the interior of the system.
Figure 2:
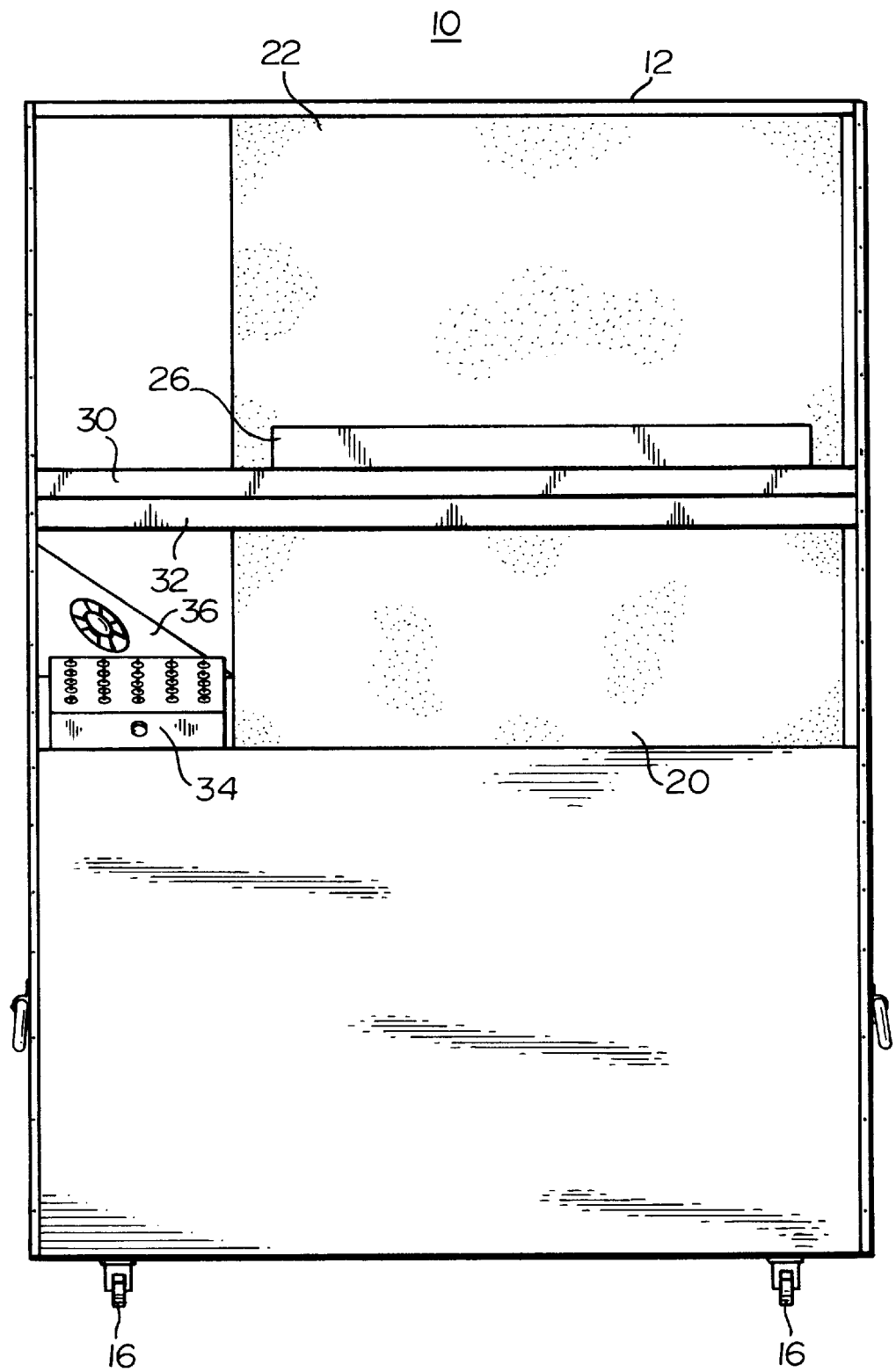
FIG. 2 is a simplified front view of the apparatus.

Turning to FIGS. 1 and 2, the apparatus 10 for selectively providing light of different shades as an aid in designing interiors of the present invention is a display arrangement especially designed to help an aircraft interior designer select the best color of fluorescent lamp to match the chosen fabric and decor of the cabin, vanity, galley, etc. More broadly, the appartus 10 could be used to select lights for use with wall paper, curtains, or other patterned sheet material used for interior decoration of a room in a building (as opposed to a cabin or other room of an airplane).

The housing 12 is a box or cabinet made with ¼" black plastic panels and having an operator side 14 at which a human operator (not shown) may sit in order to view fabric illuminated under lights. The operator side 14 is open, whereas the other sides and top and bottom of the housing 12 are closed to minimize the amount of outside light that can enter the interior of housing 12.

The apppartus 10 has four caster wheels 16 and two handles 18, one at each of two opposing sides. In the preferred embodiment of appartus 10, the outside dimensions are: Height 1700 mm (67")

Width 1050 mm (41")

Depth 700 mm (28")

Interior of the housing are lower panel 20 and top panel 22 which are cork panels (or other tack boards) on which fabric samples can easily be stretched and held in place with thumbtacks. It is important that any fabrics be held tightly to the panel in order to most realistically simulate how they will appear in use. The lower panel 20 can be considered as a first panel, whereas the top panel 22 can be considered as a second panel.

The top panel 22 has an up-wash lighting provided by one fluorescent upwash lamp 24 (length: 950 mm; 37.4") disposed in an L channel trough 26 that blocks light from lamp 24 going directly toward the operator side 14.

The lower panel 20 is inclined at a 15 degree angle relative to horizontal and provides a good viewing for an operator sitting in front of the display as well as for a person standing behind the operator. This shelf or panel 20 is illuminated by five fluorescent downwash lamps 28 (length: 950 mm; 37.4") mounted to the lower side of a light shield 30 having downwardly extending edge 32, which edge 32 blocks light from lamps 28 from going directly in the direction of the operator side 14.

A control panel 34 includes switches and a dimmer to allow the operator to turn on and off the lights and to dim them. Electrical box 38 is electrically connected to the lamps 24 and 28 via the control panel (also controller or switch box) 34. For the comfort of the operator a fan 36 can be turned on. An aerator can change the direction of the airflow.

The apparatus preferably has a set of six different shades of white. However, the apparatus alternately could be used for selecting among different colors of lights other than white. As used herein, shades of lights shall include shades of a common color (e.g., different shades of white) and also include different colors (i.e., green light is a different shade than blue light).

Preferably, six light bulbs having degree K ratings of 3,000; 3,500; 4,200; 4,500; 5,000; and 6,500 are used.

All bulbs are easily removed and replaced with another color bulb if desired as both 24 and 28 may be standard fluorescent light fixtures.

Among the specifics of some of the parts for the preferred embodiment are the following:

22—Top Panel for Attaching Fabric to View With Up-Wash;

28—Lamp 914.4 mm×609.6 mm (36"×24")

24—Flouresent Lamp for Illuminating Fabric On Top Cork Board—977.9 mm LONG (38.5")

30—Light Shield For Illuminating Fabric On Lower Cork Panel—Full Width 1012.8 mm (39.875")

34—Switch Box for Controlling Lights (On/Off—Dimming) and Fan (On/Off)—Mounted to Left Side as shown or Right Side 20—Lower Cork Panel for Attaching Fabric to View With Down-Wash Lighting System—1012.8 mm×558.8 mm (39.875"×22")

Figure 3:
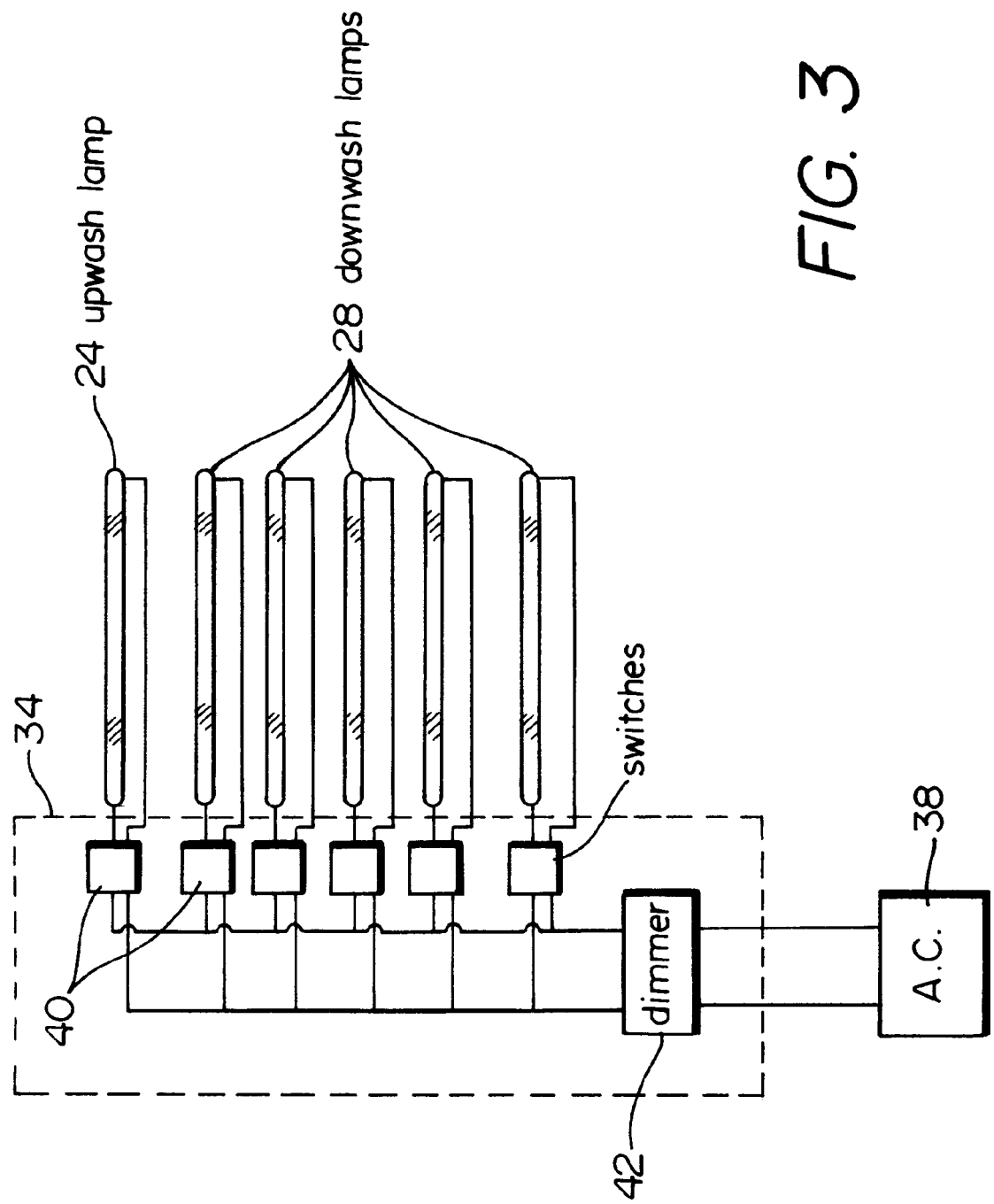
FIG. 3 is a simplified schematic of the electrical parts of the apparatus.

Main Body of Housing 12 or Cabinet Made With 6.35 mm (¼") Thick Black Plastic Panels—Smooth Inside/Embossed Outside The electrical system is shown in FIG. 3 where the upwash lamp 24 and downwash lamps 28 are connected via controller 34 to electrical box 38 (in turn receiving AC from a wall outlet. The controller 34 has switches 40 and dimmer 42 to selectively turn on the lamps.

The use of the apparatus 10 has the operator tack some fabric on the lower panel 20. Using the switches 40 of the controller 34 the operator selectively turns on each of the lamps 28 in turn, the lamps illuminating the fabric with different shades of light. The dimmer 42 can be used to adjust the intensity of the light. Upon selecting a particular shade of light as the best shade for the fabric being matched, the fabric is placed on the upper panel 22. A bulb of the selected shade is inserted into lamp 24 and it is turned on. This allows the operator to verify that the light shade selected by the downwash illumination is proper and works well for the upwash display.

Although specific constructions have been presented herein, it is to be understood that these are for illustrative purposes only. Various modifications and adaptations will be apparent to those of skill in the art. In view of possible modifications, it will be appreciated that the scope of the present invention should be determined by reference to the claims appended hereto.

What is claimed is:

1. An apparatus for selectively providing light of different shades as an aid in designing interiors comprising:

a housing having an interior and open at least partly on an operator side;

first panel interior to the housing and operable to selectively hold patterned sheet material;

a plurality of light sources supported by the housing, each light source operable to output a corresponding shade of light; and a controller operably connected to the housing and operably to selectively turn on the light sources one at a time such that any patterned sheet material on the first panel is illuminated by the shade of light corresponding to the light source turned on at a given moment; and wherein the light sources include at least one unwash light source positioned to light patterned sheet material removably secured to the housing, the upwash light source shining light on the patterned sheet material from below the patterned sheet material; and at least one downwash light source positioned to light patterned sheet material removably secured to the housing, the downwash light source shining light on the patterned sheet material from above the patterned sheet material; and further comprising a second panel interior to the housing and operable to selectively hold patterned sheet material and wherein the upwash light source is positioned to illuminate any patterned sheet material placed on the second panel and the downwash light source is positioned to illuminate any patterned sheet material placed on the first panel.

2. The apparatus of claim 1 wherein the downwash light source is one of a plurality of downwash light sources, each of which is positioned to illuminate any patterned sheet material placed on the first panel.

3. The apparatus of claim 2 wherein the first panel extends downward toward the operator side and wherein the second panel extends upward toward the operator side.

4. The apparatus of claim 3 wherein the housing is enclosed on all sides other than the operator side.

5. The apparatus of claim 4 wherein the first panel is a tack board and the second panel is a tack board.

6. The apparatus of claim 4 wherein the housing has a height of at least 4 feet.

7. The apparatus of claim 4 further including a fan in the housing for providing air flow for an operator positioned just outside the housing at the operator side.

8. The apparatus of claim 4 wherein the controller is operable to dim the light sources.

9. The apparatus of claim 1 wherein the light sources output different shades of white light.

10. The interior design system of claim 9 wherein the light subsystem includes: at least one upwash light source positioned to light patterned sheet material removably secured to the housing, the upwash light source shining light on the patterned sheet material from below the patterned sheet material; and at least one downwash light source positioned to light patterned sheet material removably secured to the housing, the downwash light source shining light on the patterned sheet material from above the patterned sheet material.

11. An apparatus for selectively providing light of different shades as an aid in designing interiors comprising:

a housing having an interior and open at least partly on an operator side, the housing being enclosed on all sides other than the operator side;

first panel interior to the housing and operable to selectively hold patterned sheet material;

a light subsystem supported by the housing the light subsystem operable to selectively output different shades of light; and a controller operably connected to the housing and operably connected to the light subsystem to determine shades of light for illuminating any patterned sheet material on the first panel such that a person on the operator side may view patterned sheet material under different shades of light; and wherein the light subsystem includes: at least one upwash light source positioned to light patterned sheet material removably secured to the housing, the upwash light source shining light on the patterned sheet material from below the patterned sheet material; and at least one downwash light source positioned to light patterned sheet material removably secured to the housings the downwash light source shining light on the patterned sheet material from above the patterned sheet material; and further comprising a second panel interior to the housing and operable to selectively hold patterned sheet material and wherein the upwash light source is positioned to illuminate any patterned sheet material placed on the second panel and the downwash light source is positioned to illuminate any patterned sheet material placed on the first panel.

12. The apparatus of claim 11 wherein the downwash light source is one of a plurality of downwash light sources, each of which is positioned to illuminate any patterned sheet material placed on the first panel.

13. The apparatus of claim 12 wherein the first panel extends downward toward the operator side and wherein the second panel extends upward toward the operator side.

14. The apparatus of claim 13 wherein the housing is enclosed on all sides other than the operator side.

15. The apparatus of claim 14 wherein the first panel is a tack board and the second panel is a tack board.

16. The method of selecting lights for use with a patterned sheet material, the steps comprising:

providing an apparatus for selectively providing light of different shades as an aid in designing interiors with:

a housing having an interior and open at least partly on an operator side; first panel interior to the housing and operable to selectively hold patterned sheet material;

a plurality of light sources supported by the housing, each light source operable to output a corresponding shade of light; and a controller operably connected to the housing and operable to selectively turn on the light sources one at a time such that any patterned sheet material on the first panel is illuminated by the shade of light corresponding to the light source turned on at a given moment;

attaching a patterned sheet material on the first panel; and selectively turning the light sources in order for a person on the operator side to view light shining on the patterned sheet material; wherein the patterned sheet material is a fabric; wherein a light source that best illuminates the fabric is selected from the viewing of the fabric under different of the light sources; and wherein the light source that best illuminates the fabric is installed in a room having the fabric.

17. The method of claim 16 wherein the light source that best illuminates the fabric is installed in an aircraft interior having the fabric.

18. The method of claim 17 wherein the plurality of light sources provide different shades of white light.

* * * * *

UNITED STATES PATENT AND TRADEMARK OFFICE
CERTIFICATE OF CORRECTION

PATENT NO. : 6,092,908
DATED : July 25, 2000
INVENTOR(S) : Ladjimi

Page 1 of 1

It is certified that error appears in the above-identified patent and that said Letters Patent is hereby corrected as shown below:

Claim 1, column 5,
Line 6, delete "unwash" and insert "upwash"

Signed and Sealed this

Eighteenth Day of September, 2001

Attest:

NICHOLAS P. GODICI
Attesting Officer
Acting Director of the United States Patent and Trademark Office